United States Patent [19]

Haendle et al.

[11] 4,442,534
[45] Apr. 10, 1984

[54] X-RAY DIAGNOSTIC INSTALLATION FOR X-RAY TOMOGRAPHIC IMAGES

[75] Inventors: Joerg Haendle; Hartmut Sklebitz, both of Erlangen, Fed. Rep. of Germany

[73] Assignee: Siemens Aktiengesellschaft, Berlin & Munich, Fed. Rep. of Germany

[21] Appl. No.: 396,757

[22] Filed: Jul. 9, 1982

[30] Foreign Application Priority Data

Jul. 17, 1981 [DE] Fed. Rep. of Germany ....... 3128380

[51] Int. Cl.³ .................. A61B 6/00; H04N 5/32; H05G 1/64; H05G 1/70
[52] U.S. Cl. .......................................... 378/21; 378/22
[58] Field of Search .................. 378/21, 22, 25, 26, 378/23, 24, 27

[56] References Cited

U.S. PATENT DOCUMENTS 4,149,082 4/1979 Haendle .................. 250/445 T

Primary Examiner—Alfred E. Smith
Assistant Examiner—T. N. Grigsby
Attorney, Agent, or Firm—Hill, Van Santen, Steadman & Simpson

[57] ABSTRACT

An exemplary embodiment includes at least one x-ray tube for the generation of an x-ray beam, a patient support, an image detector, and a control generator—connected with the x-ray tube and the image detector—for the purpose of moving the x-ray beam, and in opposition thereto, the image field of the image detector. There is connected to the control generator a layer height computer which calculates the enlargement from the geometric data for the tomogram. The image detector has a circuit—connected with the layer height computer—for the purpose of fading-in a marking for the dimensions in the layer plane.

10 Claims, 3 Drawing Figures

X-RAY DIAGNOSTIC INSTALLATION FOR X-RAY TOMOGRAPHIC IMAGES

BACKGROUND OF THE INVENTION

The invention relates to an x-ray diagnostic installation for x-ray tomographic images comprising at least one x-ray tube for the generation of an x-ray beam, a patient support, an image detector and a control generator, connected with the x-ray tube and the image detector, for the purpose of moving the x-ray beam and, synchronously therewith, the image field of the image detector.

In the German OS No. 2,712,320 such an x-ray diagnostic installation is described in which, by means of a synchronous movement of the x-radiation and of the image of the image detector, designed in the form of an x-ray image intensifier, a body layer is imaged in a sharply defined fashion, whereas all other body parts not disposed in this layer are suppressed through blurring. The desired layer can be selected either through alteration of the distance of the image detector from the patient support and the x-ray tube or, in the case of an x-ray image intensifier-television chain, through alteration of the deflection of the electron image in the x-ray image intensifier. The position of the layer is determined through the distances: x-ray tube-body layer and body layer-image detector, so that varying scales of enlargement result which are unknown to the observer. Therefore, mechanical auxiliary means, for example, measuring a tape, a measuring cylinder or a measuring sphere, can be provided in the ray path in order to be able to determine therefrom the dimensions of the body parts. Due to the known geometric dimensions of these auxiliary means, via specific tables, a scale indication can be associated with each layer height. In the case of an x-ray image intensifier-television chain the deflection of the electron image in the x-ray image intensifier determines the layer height so that the dimensions of a body part are to be ascertained here also via tables or mechanical auxiliary means. However, these methods are difficult and time-consuming, so that most frequently they are not employed.

SUMMARY OF THE INVENTION

The invention proceeds from the objective of producing an x-ray diagnostic installation of the type initially cited in which values are faded into the x-ray image which form a scale so that, on the basis of these fadings-in, the dimensions of the body part can be directly ascertained.

The object is achieved in accordance with the invention in that there is connected to the control generator a layer height computer which calculates the enlargement from the geometric data for the tomogram, and that the image detector exhibits an apparatus—connected with the layer height computer—for the purpose of fading-in a marking for the dimensions in the layer plane. Due to this fading-in one obtains in the x-ray image a scale indication so that the dimensions can thus be determined.

An advantageous scale indication is obtained if the marking to be faded in represents a scale which is comprised of a stationary part, which corresponds to a standardized distance disposed parallel to the image detector plane, and of a variable part which characterizes the enlargement. A simple apparatus without parts to be moved mechanically results if, for the generation and movement of the x-ray beam, a number of x-ray tubes is present which are capable of being switched on individually in succession by means of the control generator, and if the image detector is comprised of an x-ray image intensifier with deflection coils which are connected with a deflection circuit connected to the control generator.

Indirect radiographs can be prepared if a film camera is aligned with the output fluorescent screen of the x-ray image intensifier, and if the apparatus effects with optical means an exposure of the marking on the film. A simple arrangement is achieved if, for the purpose of photographic exposure of the scale, a luminescent diode chain is present, if the one part of the luminescent diode chain, which corresponds to the calibrated length, is always photographically exposed, and if the second part of the luminescent diode chain, which characterizes the enlargement, is controlled by a voltage which is proportional to the amplitude of the deflection of the electron image in the x-ray image intensifier.

An electronic fading-in into the television image can proceed if a television camera is coupled with the optical output of the x-ray image intensifer, a mixing stage is provided to which the output signals of the apparatus are supplied, and if a monitor is connected to the output of the mixing stage. An alternative solution is achieved if the enlargement or the scale is digitally calculated in the layer height computer and faded into the television image as a numerical value.

The invention shall be explained in greater detail in the following on the basis of an exemplary embodiment illustrated in the Figures on the accompanying drawing sheets; and other objects, features and advantages will be apparent from this detailed disclosure and from the appended claims.

DETAILED DESCRIPTION

Figure 1:
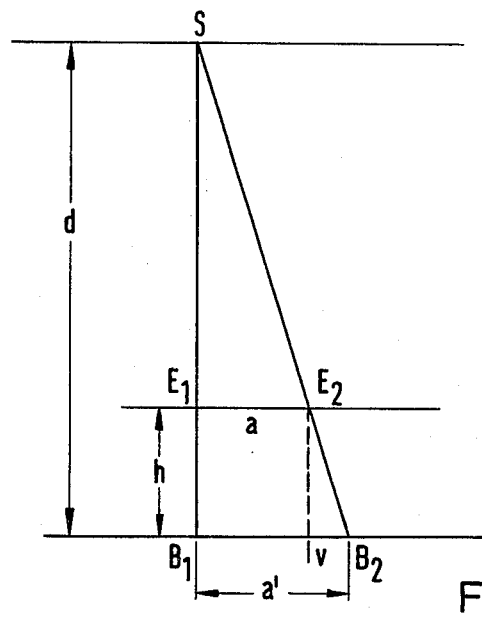
FIG. 1 shows a graphic illustration for the purpose of explaining the inventive idea.

On the basis of FIG. 1, the enlargement within an x-ray beam is now explained. In the radiator plane there is disposed an x-ray radiator S which emits a radiation beam to the image detector-plane, of which two rays $\overline{SB}_1$ and $\overline{SB}_2$ are illustrated. These two rays bound or delimit at the points $E_1$ and $E_2$, a distance a in the layer plane which is disposed parallel to the image detector plane. The distance of the x-ray radiator S relative to the image detector is characterized by the distance d. The layer plane lies at a height h above the image detector. The distance a', imaged in the image detector plane, can be calculated from the ray set:

$$a' = \frac{d \cdot a}{d - h} \quad (1)$$

The distance a' can be expressed as a distance a enlarged by the extension v. The extension then results from:

$$v = a' - a \quad (2)$$

If one inserts (1) into (2), one then obtains:

$$v = \frac{d \cdot a}{d-h} - a \qquad (3)$$

Following solution of the equation there results for the extension:

$$v = a\frac{h}{d-h}. \qquad (4)$$

Thus, the imaged distance can be expressed by a distance a, disposed in the layer plane, which distance a can, for example, by standardized, and by an extension v. This is utilized, in case of the fading-in of the scale, in such a manner that the fading-in exhibits a fixed component (a) and a variable component (v).

Figure 2:
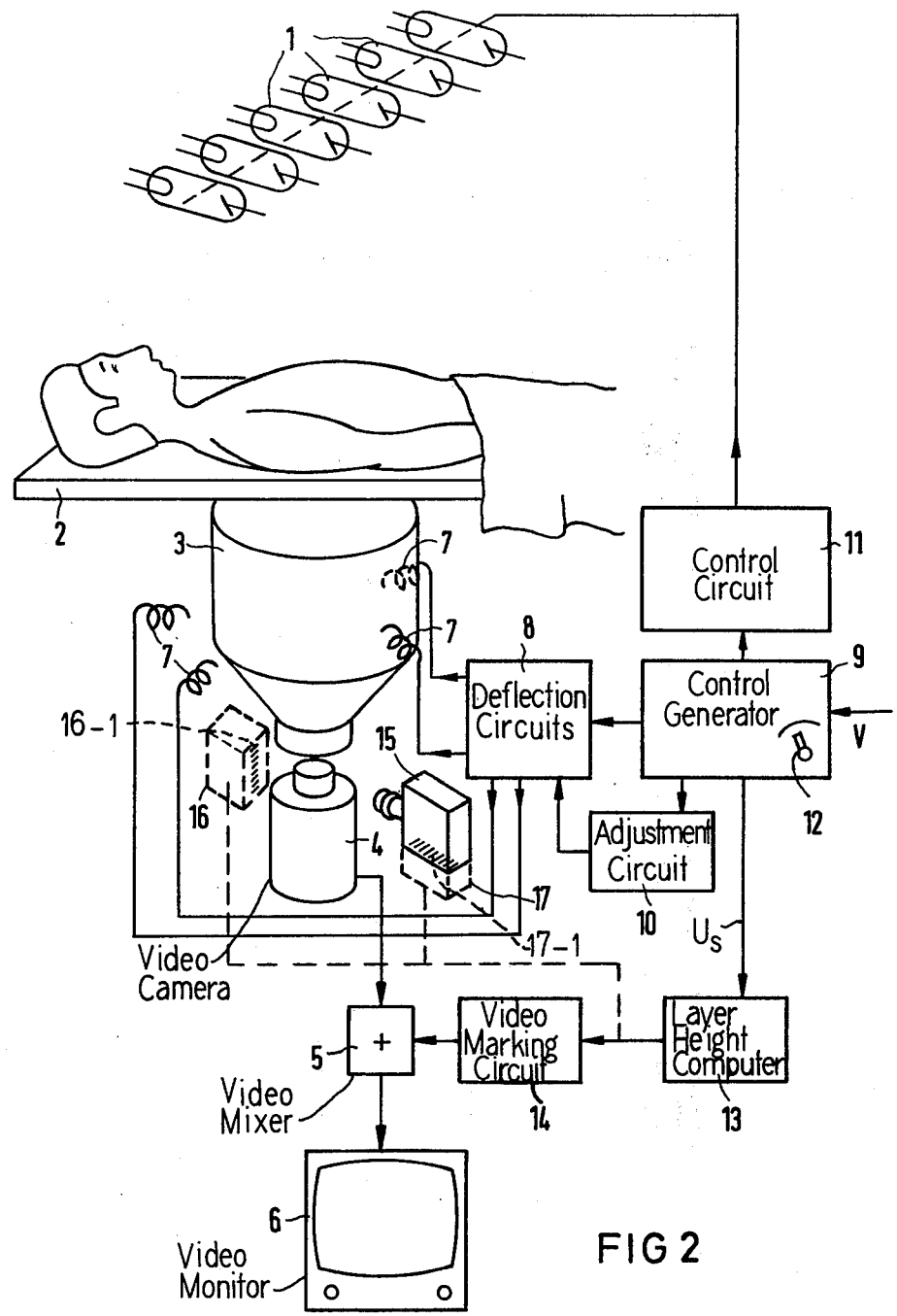
FIG. 2 shows an x-ray diagnostic installation according to the invention.

In FIG. 2, an x-ray diagnostic installation is illustrated which exhibits six x-ray tubes 1 arranged in a series which are provided with control grids. For the purpose of simplicity, the high voltage transformer for the x-ray tubes 1 is not illustrated. The x-ray tubes 1 generate x-ray beams which penetrate a patient lying on a patient support 2 and which cast radiation images on the inlet fluorescent screen of an x-ray image intensifier 3. The output image of the x-ray image intensifier 3 is picked up by a television camera 4 and supplied to a monitor 6 via a mixer 5.

The electron image of the x-ray image intensifier 3 is magnetically deflected by means of two pairs of deflection coils 7. The activation of the deflection coils proceeds by means of a deflection circuit 8 which is synchronized by a control generator 9. The position displacement necessary for the tomogram selection is effected by means of a position adjustment circuit 10. The control generator 9 effects, synchronously with the image displacement in the x-ray image intensifier 3, the step-wise switching-on of the x-ray tubes 1 via a control circuit 11 to which the grids of the x-ray tubes 1 are connected. The vertical pulses V of the television system are supplied to the control generator 9. An adjustment means 12, secured to the control generator 9, which adjustment means can be designed as a potentiometer, serves the purpose of selection of the layer height.

The control generator 9 causes the x-ray beam emanating from the x-ray tubes 1 to be moved, through a step-wise switching-on of one of the x-ray tubes 1 at a time, and actuates the displacement circuit 10 and the deflection circuit 8 such that the electron image in the x-ray image intensifier 3 is moved oppositely in relation thereto, so that only the parts lying in a specific body longitudinal layer, determined by the pivot axis of the x-ray beam, are imaged on the monitor 6 in a sharply defined fashion, whereas the details lying outside this specific body longitudinal layer are rendered in a blurred fashion.

The body layer whose details are represented on the monitor 6 in a sharply defined fashion can be selected, in addition to selection by change of the magnetic image deflection, also by adjustment of the distance between the x-ray tubes 1 and the patient support 2 as well as by adjustment of the distance between the x-ray image intensifier 3 and the patient support 2.

For the fading-in of a scale a layer height computer 13 is connected to the control generator 9, said computer calculating the scale from the geometric dimensions and the deflection selected by the adjustment means 12. Connected to the layer height computer 13 is a circuit 14 whose output is connected with the second input of the mixer 5.

Figure 3:
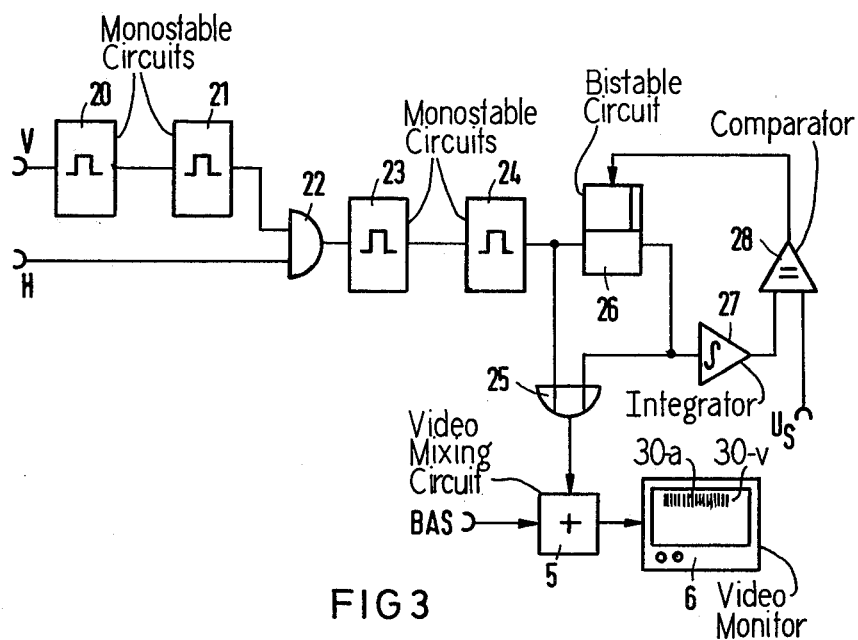
FIG. 3 shows an exemplary embodiment of a circuit for the x-ray diagnostic installation according to FIG. 2.

On the basis of FIG. 3, the method of operation of the circuit 14 shall now be explained in greater detail. This circuit fades a bar as a scale into the television image. The vertical pulses V of the television system are supplied to a first monostable flip-flop 20 whose output is connected to a second monostable flip-flop 21. The output of the second monostable flip-flop 21 is connected with the first input of an AND circuit 22, to the second input of which the horizontal pulses H of the television system are supplied. Connected to the output of the AND circuit 22 is a series connection of a third and of a fourth monostable flip-flop 23 and 24. The output signal of the fourth monostable flip-flop 24 is supplied to the one input of an OR circuit 25 and to the set input of a D flip-flop 26. The output of the D flip-flop 26 is connected with the other input of the OR circuit 25. Simultaneously, the output signal of the D flip-flop 26 is supplied to an integrator 27 whose output signal is compared in a comparator 28 with a voltage $U_S$. This voltage $U_S$ is generated in the layer height computer 13 and is proportional to the amplitude of the deflection of the electron image in the x-ray image intensifier 3. The output of the comparator 28 is connected with the reset input of the D flip-flop 26. The output signal of the OR circuit 25 is superimposed in the mixing stage 5 with the composite video signal (BAS) coming from the television camera 4 and is displayed on the monitor 6.

The delay time of the first monostable flip-flop 20 determines the vertical position of the faded-in scale in the image. The first monostable flip-flop 20 triggers the second monostable flip-flop 21 which determines how many lines high the scale is. The second monostable flip-flop enables the AND circuit 22 and thus throughconnects the horizontal pulses to the third monostable flip-flop 23 which determines a horizontal position of the scale. The fourth monostable flip-flop 24, triggered by the third monostable flip-flop 23, determines the length of the standard scale which corresponds to the distance a. The fourth monostable flip-flop 24 sets the D flip-flop 26 whose output releases the integrator 27. The rising output voltage of the integrator 27 is compared with the voltage $U_S$ in the comparator 28. The voltage $U_S$ is proportional to the extension v. When the output voltage of the integrator 27 corresponds to the voltage $U_S$, the D flip-flop 26 is reset. The output signals of the fourth monostable flip-flop 24 and the D flip-flop 26 are combined in the OR circuit 25 and displayed, via the mixing stage 5, on the monitor 6 in the form of a scale.

Instead of a scale fading-in, the enlargement can be digitally calculated in the layer height computer 13 and can be faded-in as a numerical value into the television image.

If indirect tomograms are to be prepared, then, as illustrated in FIG. 2, a film camera 15 is coupled, via a non-illustrated optics, to the output fluorescent screen of the x-ray image intensifier 3. Via a semitransmissive mirror, a luminescent diode chain, arranged in a device 16, can be jointly exposed on the film. The luminescent diode chain of the device 16 is controlled by the layer height computer 13. The luminescent diode chain consists of a fixed part which is always jointly exposed, and a variable part which corresponds to the extension v. This activation of the variable part can, for example, proceed through integrated modules of the type UAA 180 which are subjected to the voltage $U_S$.

The scale can, however, also be exposed by means of an additional device 17 applied on the film camera 15. This additional device 17 likewise exhibits a luminescent diode chain. It is directly arranged on the film of the film camera 15 and is switched on during the exposure.

The invention is not restricted to the described exemplary embodiment; on the contrary, it is applicable also in the case of tomographs in which a mechanical synchronous movement of an x-ray radiator and an image layer takes place.

Through the inventive apparatus one obtains x-ray tomographic images into which a scale is faded, so that the size of body parts disposed in the layer plane can be directly determined.

It will be apparent that many modifications and variations may be effected without departing from the scope of the novel concepts and teachings of the present invention.

SUPPLEMENTAL DISCUSSION

The disclosure of the Haendle et al. U.S. Pat. No. 4,149,082 issued Apr. 10, 1979 is incorporated herein by reference by way of background. This patent shows exemplary detailed circuitry for components 8 through 11 of FIG. 2 of the present disclosure.

Referring to the sixth figure of U.S. Pat. No. 4,149,082, the value of the output of potentiometer twenty-seven represents the value of the selected layer height and may be connected with the layer height computer 13. This potentiometer twenty-seven may be coupled with control knob 12 of the control generator.

For the sake of exemplary illustration, a black bar is indicated at 30a on the screen of monitor 6 in FIG. 3 whose height is controlled by the time constant of monostable 21 and whose length is controlled by monostable 24 to represent the length a in the layer plane. The system of FIG. 2 may be operated so that the length of bar 30a represents a standarized distance, and the parameters of integrator 27 may be adjusted so as to represent the varying scale of enlargement in relation to such standarized distance. The length of bar 30v on the screen of monitor 6 in FIG. 3 represents the timing of the output from comparator 28 in FIG. 3 in relation to the black bar 30a (for each horizontal line sync pulse transmitted by gate 22). Where the time constant of monostable 24 is maintained at a fixed value, the length of bar 30a will be a constant value on the screen of monitor 6. If the bistable circuit 26 is triggered by a negative going edge of the output of monostable 24, the integrator 27 will be turned on at the conclusion of each line portion of bar 30a. The output of the bistable circuit 26 will produce a portion of bar 30v in a time interval representing the magnitude of the layer height adjustment $U_S$. The OR gate 25 may be actuated to produce the bar 30v until the output pulse from bistable 26 will be zero in response to the comparison output from comparator 28.

More generally, the layer height computer 13, FIG. 2, may receive input data representing the geometry of the system such as the distance d between the source plane S and the input screen of the x-ray image intensifier, and the angular relationships between the x-ray beam axes and the axis of the x-ray image intensifier, as well as the layer height setting.

Referring to FIG. 2, a luminescent diode chain is indicated at 16-1 in association with device 16. A similar diode chain is indicated at 17-1 in association with device 17. One portion of each diode chain produces an optical bar such as indicated at 30a in FIG. 3, while further luminescent diodes produces an optical bar such as the bar 30v in FIG. 3.

We claim as our invention:

1. An x-ray diagnostic installation for x-ray tomographic images, comprising x-ray source means (1) for the generation of an x-ray beam, a patient support (2), an image detector (3) and a control generator (9), connected with the x-ray source means (1) and the image detector (3), for the purpose of movement of the x-ray beam and, synchronously thereto, of the image field of the image detector (3), characterized in that a layer height computer (13) is connected to the control generator (9) for calculating the enlargement from the geometric data for the tomogram, and that the image detector (3) has circuit means (14, 16) connected with the layer height computer (13) for fading-in a marking for representing the dimensions in the layer plane.

2. An x-ray diagnostic installation according to claim 1, characterized in that the circuit means produces a marking to be faded in which represents a scale including a stationary part, which corresponds to a standardized distance (a) disposed parallel to the image detector plane, and including a variable part which characterizes the enlargement (v).

3. An x-ray diagnostic installation according to claim 1 characterized in that, for the generation and movement of the x-ray beam, said x-ray source means comprises a number of x-ray sources (1) which are capable of being switched on individually in succession by means of the control generator (9), and that the image detector comprises an x-ray image intensifier (3) which is surrounded by deflection coils (7), and a deflection circuit (8) connected to the deflection coils (7) and controlled by said control generator (9) so as to shift the image field of the image intensifier in step with the switching on of successive ones of said x-ray sources (1).

4. An x-ray diagnostic installation according to claim 3, characterized in that a film camera (15) is optically coupled with the output flourescent screen of the x-ray image intensifier (3), and that the circuit means (16) has optical means for effecting an exposure of the marking on the film.

5. An x-ray diagnostic installation according to claim 4, characterized in that the optical means comprises a luminescent diode chain for the purpose of effecting an exposure of the marking on the film.

6. An x-ray diagnostic installation according to claim 5, characterized in that the luminescent diode chain has one part thereof which corresponds to a calibrated length which one part is activated for each exposure and has a second part which characterizes the enlargement, said circuit means being controlled by a voltage ($U_S$) which is proportional to the amplitude of the deflection of the electron image in the x-ray image intensifier (3), to select the activation of the second part of the luminescent diode chain according to the amplitude of said deflection during an exposure.

7. An x-ray diagnostic installation according to claim 3, characterized in that a television camera (4) is coupled with the optical output of the x-ray image intensifier (3), said circuit means (14) having a mixing stage (5) connected to receive the output signals of the circuit means (14) and of the television camera (4), and a video monitor (6) connected to the output of the mixing stage (5).

8. An x-ray diagnostic installation according to claim 7, characterized in that the circuit means comprises a first monostable flip-flop (20) to which the vertical pulses are supplied, a second monostable circuit (21) being connected to the first monostable circuit (20), an AND circuit (22) having a first input subjected to video line repetition rate pulses, having a second input connected to the output of the second monostable circuit (21), and having an output, a series-connection of a third and of a forth monostable circuit (23, 24) connected with the output of said AND circuit (22), an OR circuit (25) connected with the forth monostable circuit (24), bistable means (26) having a set input connected with the output of the forth monostable circuit (24) and having an output connected with an input of the OR circuit (25), an integrator (27) connected to the output of the bistable means (26), and a comparator (28) having a first input connected to receive a voltage ($U_S$) which is proportional to the amplitude of the deflection of the electron beam in the x-ray image intensifier (3), having a second input connected with the output of the integrator (27), the bistable means (26) having a reset input connected with the output of the comparator (28), and the output signal of the OR circuit (25) being supplied to the mixing stage (5).

9. An x-ray diagnostic installation according to claim 7, characterized in that the marking is digitally calculated in the layer height computer (13) and is faded into the display of the video monitor (6) as a numerical value.

10. An x-ray diagnostic installation according to claim 2, with the image detector comprising an x-ray image intensifier having an optical output for supplying an optical image representing the tomogram, a video camera coupled with the optical output of the x-ray image intensifier for converting the optical image into a video image signal, and mixing means connected with the output of the video camera and with the layer height computer and operable for superimposing a video marking signal in accordance with the marking to be faded in on the video image signal to provide for the joint recording of the tomogram and the marking representing the dimension in the layer plane.

* * * * *